US009345606B2

(12) United States Patent
Bonutti et al.

(10) Patent No.: US 9,345,606 B2
(45) Date of Patent: *May 24, 2016

(54) SHOULDER ORTHOSIS

(71) Applicant: Bonutti Research, Inc., Effingham, IL (US)

(72) Inventors: Peter M. Bonutti, Effingham, IL (US); Christopher A. Leo, Effingham, IL (US); Kevin R. Ruholl, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,883

(22) Filed: Oct. 30, 2013

(65) Prior Publication Data

US 2014/0171846 A1 Jun. 19, 2014

Related U.S. Application Data

(60) Continuation of application No. 13/155,132, filed on Jun. 7, 2011, now Pat. No. 8,591,442, and a continuation of application No. 10/760,598, filed on Jan. 20, 2004, now Pat. No. 7,955,285, and a continuation of application No. 10/626,951, filed on Jul. 25, 2003, now Pat. No. 6,929,616, and a continuation of application No. 09/579,038, filed on May 26, 2000, now Pat. No. 6,599,263, and a division of application No. 09/088,134, filed on Jun. 1, 1998, now Pat. No. 6,113,562.

(51) Int. Cl.
*A61F 5/00* (2006.01)
*A61F 5/01* (2006.01)
*A61F 5/058* (2006.01)
*A61H 1/02* (2006.01)

(52) U.S. Cl.
CPC ............... *A61F 5/0102* (2013.01); *A61F 5/013* (2013.01); *A61F 5/05858* (2013.01); *A61H 1/0281* (2013.01)

(58) Field of Classification Search
CPC ......... A61F 5/0102; A61F 5/013; A61F 5/02; A61F 5/05858; A61F 5/3738; A61F 13/02; A61F 13/15593; A61F 13/15609; A61F 5/00; A61F 5/01; A61F 5/0104; A61F 5/0118; A61F 5/022; A61F 5/024
USPC .............................. 602/4, 16, 20–22; 128/880
See application file for complete search history.

(56) References Cited

U.S. PATENT DOCUMENTS

| 2,535,489 | A | * | 12/1950 | Edwards | 623/24 |
| 4,180,870 | A | * | 1/1980 | Radulovic et al. | 623/26 |
| 4,669,451 | A | * | 6/1987 | Blauth et al. | 601/33 |
| 5,033,461 | A | * | 7/1991 | Young et al. | 602/16 |
| 5,052,379 | A | | 10/1991 | Airy et al. | |

(Continued)

*Primary Examiner* — Michael Brown
(74) *Attorney, Agent, or Firm* — Senniger Powers LLP

(57) ABSTRACT

A shoulder orthosis is utilized to effect relative movement between bones in a body of a patient. The orthosis includes a base section which is connected with a trunk of a patient's body, an upper arm section which is connected with an upper portion of an arm of the patient, and a lower arm section which is connected with a lower portion of the arm of a patient. An interconnection between the base section and upper arm section of the orthosis is disposed beneath an axilla between the trunk and arm of the patient. A main drive assembly is operable to rotate the lower arm section of the orthosis relative to the upper arm section of the orthosis to pivot a humerus bone in the upper arm of the patient relative to a scapula bone in a shoulder of the patient. A secondary drive assembly is operable to move the lower arm section and upper arm section relative to the base section of the orthosis to move the upper arm of the patient into alignment with the shoulder of the patient.

11 Claims, 6 Drawing Sheets

(56) References Cited

U.S. PATENT DOCUMENTS

| | | |
|---|---|---|
| 5,437,619 A | 8/1995 | Malewicz et al. |
| 5,472,410 A | 12/1995 | Hamersly |
| 5,520,620 A | 5/1996 | Johnson |
| 5,575,764 A | 11/1996 | Van Dyne |
| 5,749,840 A | 5/1998 | Mitchell et al. |
| 6,001,075 A | 12/1999 | Clemens et al. |
| 7,473,234 B1 | 1/2009 | Weltner et al. |
| 7,517,330 B2 | 4/2009 | Deharde et al. |
| 7,955,285 B2 * | 6/2011 | Bonutti et al. .......... 602/16 |
| 8,591,442 B2 * | 11/2013 | Bonutti et al. .......... 602/16 |

* cited by examiner

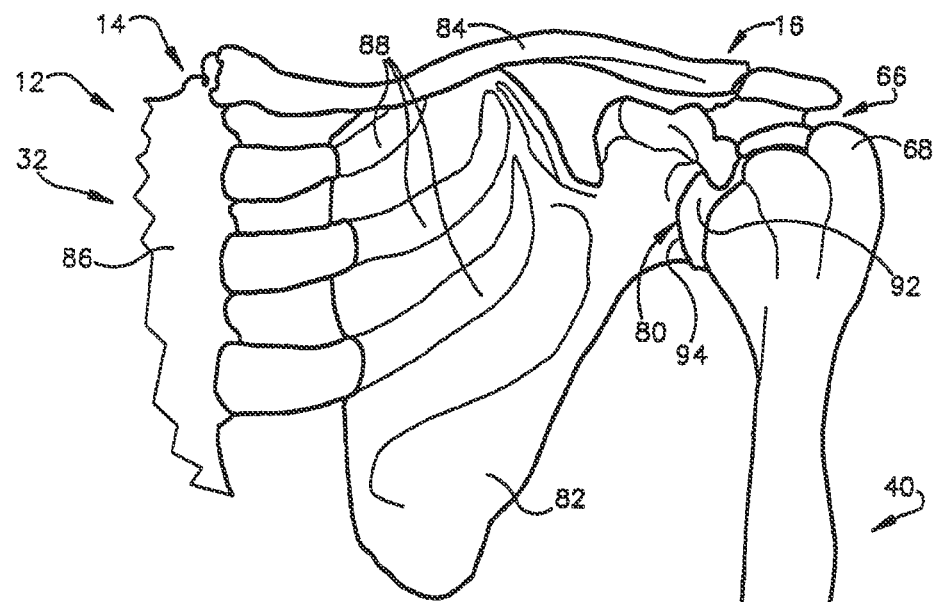
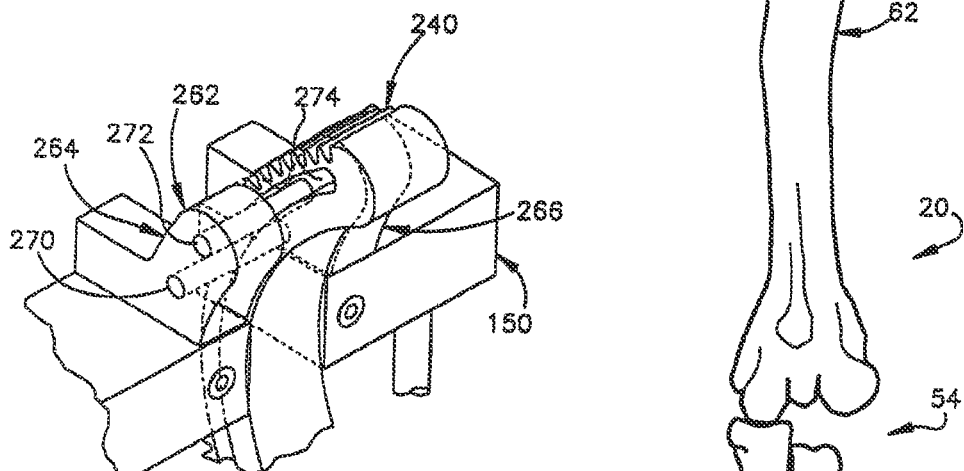
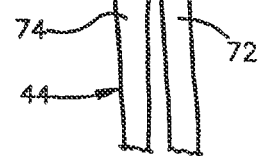

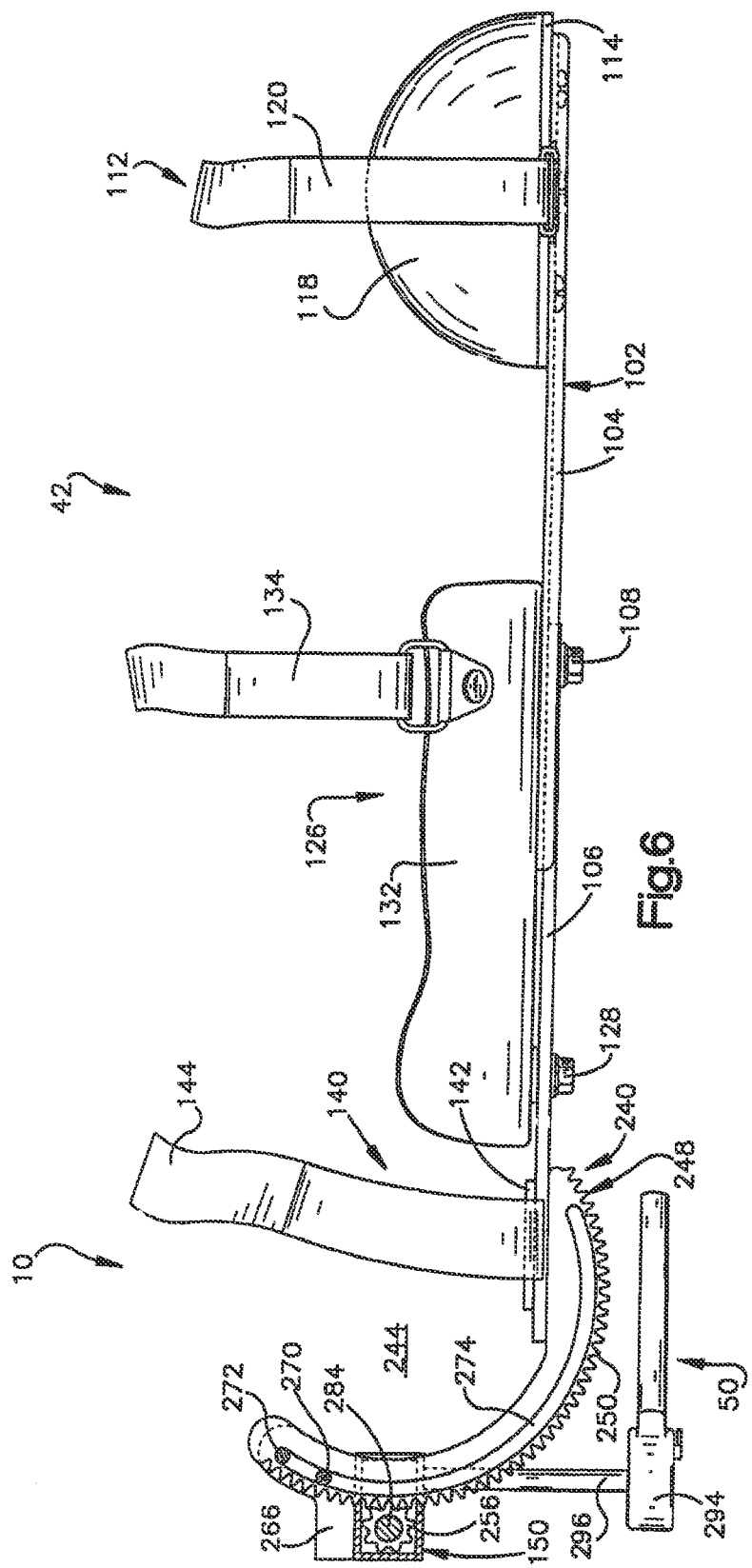

SHOULDER ORTHOSIS

CROSS REFERENCE TO RELATED APPLICATIONS

This application is a continuation of U.S. patent application Ser. No. 13/155,132, filed Jun. 7, 2011, which is a continuation of U.S. patent application Ser. No. 10/760,598, filed Jan. 20, 2004, now U.S. Pat. No. 7,955,285, which is a continuation of U.S. patent application Ser. No. 10/626,951, filed Jul. 25, 2003, now U.S. Pat. No. 6,929,616, which is a continuation of U.S. patent application Ser. No. 09/579,038, filed May 26, 2000, now U.S. Pat. No. 6,599,263, which is a divisional of U.S. patent application Ser. No. 09/088,134, filed Jun. 1, 1998, now U.S. Pat. No. 6,113,562.

BACKGROUND OF INVENTION

The present invention relates to an apparatus for use in effecting relative movement between bones in a body of a patient and, more specifically, to an apparatus for effecting movement of bones in an arm of the patient relative to a shoulder of the patient.

An orthosis for stretching viscoelastic or soft tissue in a human body to regain joint movement and eliminate tissue contracture is disclosed in U.S. Pat. No. 5,285,773. The apparatus disclosed in this patent includes a pair of cuffs which are mounted on cuff arms. A drive assembly interconnects the cuff arms.

Another orthosis is disclosed in U.S. Pat. No. 5,503,619. The orthosis disclosed in this patent includes a pair of cuffs which are connected with cuff arms. A drive assembly interconnects the cuff arms. The orthosis disclosed in the aforementioned U.S. Pat. No. 5,503,619 is particularly well adapted for use in bending a patient's wrist.

An orthosis for effecting relative movement between bones in an arm of a patient is disclosed in U.S. patent application Ser. No. 08/683,196, filed Jul. 18, 1996 by Peter M. Bonutti et al. and entitled "Orthosis". The orthosis disclosed in the aforementioned U.S. patent application includes a first cuff which grips a wrist portion of the arm of a patient. A second cuff grips an upper portion of the arm of the patient. A drive assembly is provided to rotate the first cuff about an axis which extends along the lower portion of the arm of the patient. Operation of the drive assembly effects pronation and suppination of the hand of the patient.

SUMMARY OF THE INVENTION

A new and improved apparatus for effecting relative movement between bones in a body of a patient includes a first cuff which grips a lower portion of an arm of the patient. A second cuff grips an upper portion of the arm of the patient. A drive assembly is operable to rotate the first cuff and a humerus bone in the arm of the patient about a central axis of the humerus bone. This results in a stretching of viscoelastic tissue connected with a head end portion of the humerus bone.

The extent of stretching of the viscoelastic tissue connected with a humerus bone in the arm of the patient may be maximized by interrupting operation of the drive assembly to allow the viscoelastic body tissue to relax. After the viscoelastic body tissue has relaxed, the drive assembly is again operated to further rotate the first cuff and further stretch the viscoelastic body tissue connected with the humerus bone.

A secondary drive assembly is provided to pivot the humerus bone in the arm of the patient about the head end portion of the humerus bone. This moves an arcuate surface on the head end portion of the humerus bone into alignment with an arcuate surface of a glenoid cavity in a scapula bone in the shoulder of the patient. The secondary drive assembly is disposed beneath an axilla between the trunk and arm of the patient.

BRIEF DESCRIPTION OF THE DRAWINGS

The foregoing and other features of the present invention will become more apparent upon a consideration of the following description taken in connection with the accompanying drawings wherein:

FIG. 4 is a schematic illustration depicting bones in an arm and shoulder of a patient;

FIG. 6 is a fragmentary elevational view, taken generally along the line 6-6 of FIG. 3, illustrating a lower cuff arm and a portion of the main drive assembly in the shoulder orthosis of FIGS. 1-3; and FIG. 7 (on sheet 4 of the drawings) is a fragmentary pictorial illustration of the manner in which a main gear in the drive assembly is mounted on a cuff arm of the orthosis of FIGS. 1-3.

DETAILED DESCRIPTION OF THE INVENTION

Figure 1:
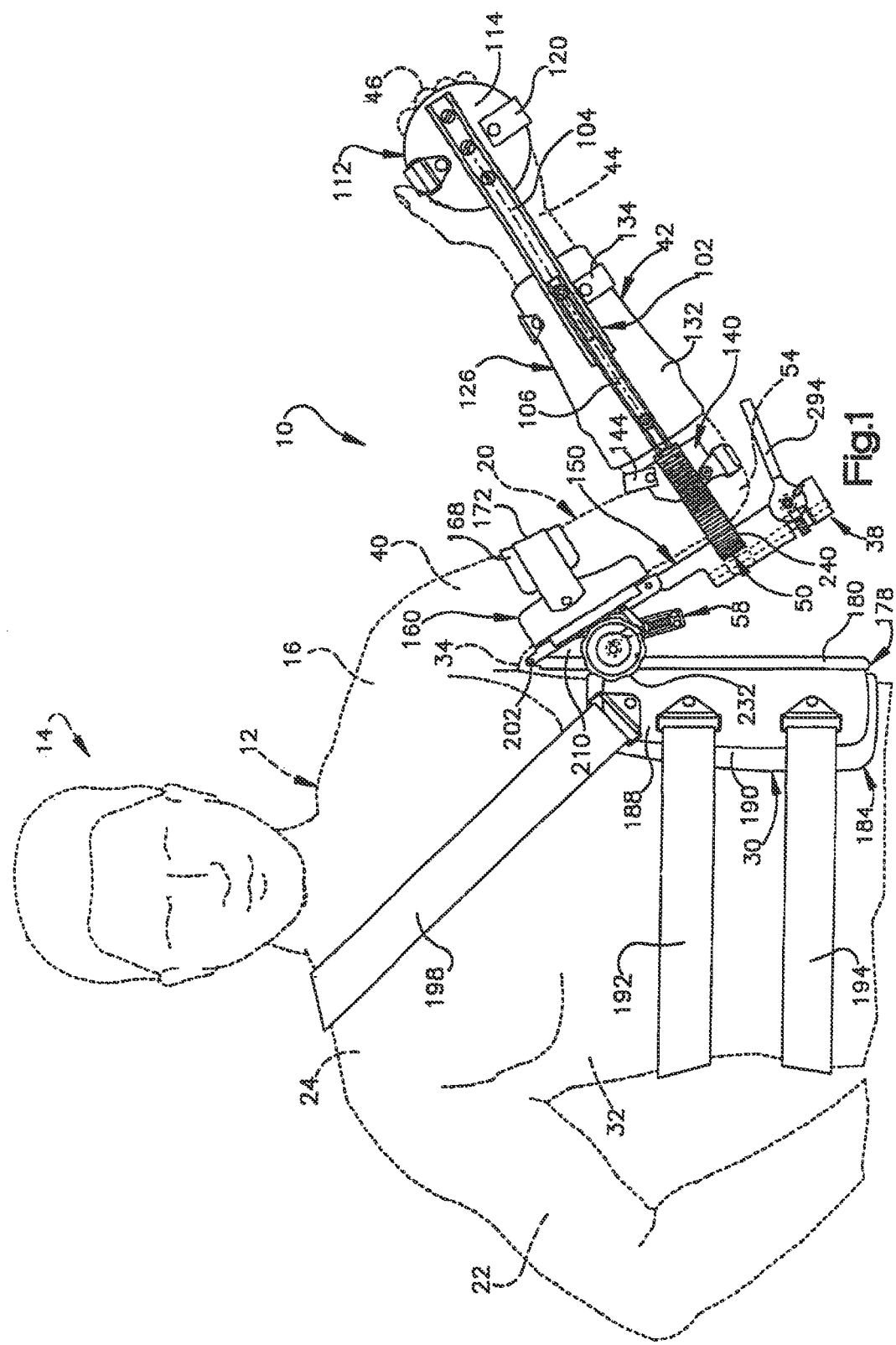
FIG. 1 is a schematic pictorial illustration depicting the manner in which a shoulder orthosis constructed in accordance with the present invention is connected with an arm and trunk of a body of a patient.

A shoulder brace or orthosis 10 (FIGS. 1-3) effects relative movement between bones in a body 12 (FIG. 1) of a patient 14. The shoulder orthosis 10 is used to correct misalignment or malfunction of joints in a shoulder 16 of a patient. Although the shoulder orthosis 10 has been illustrated in FIG. 1 as being utilized in association with a left arm 20 and shoulder 16, the shoulder orthosis 10 could be constructed for use with a right arm 22 and shoulder 24 of the patient 14 if desired.

The shoulder orthosis 10 includes a base section 30 (FIGS. 1-3) which is connected with a trunk 32 (FIG. 1) of the patient's body. The base section 30 is connected with the trunk 32 of the patient's body at a location beneath an armpit or axilla 34. The axilla 34 is formed at the connection between the left arm 20 and left shoulder 16.

The shoulder orthosis 10 includes an upper arm section 38 (FIGS. 1-3) which is connected with the upper arm section 40 (FIG. 1) of the left arm 20 of the patient. A lower arm section 42 (FIGS. 1-3) of the shoulder orthosis 10 is connected with a lower arm section 44 (FIG. 1) of the left arm 20 and a hand 46 of the patient 14.

A main drive assembly 50 (FIGS. 1-3) interconnects the upper arm section 38 and the lower arm section 42. The main drive assembly 50 is manually operable by the patient 14 (FIG. 1) to move the lower section 44 of the arm 20 relative to the upper section 40 of the arm 20. The main drive assembly 50 is located adjacent to an elbow 54 which interconnects the upper and lower sections 40 and 44 of the arm 20.

The main drive assembly 50 is operable to rotate bones in the arm 20 of the patient 14 relative to the shoulder 16 of the patient. Operation of the main drive assembly 50 rotates the bones in the arm 20 of the patient 14 about a longitudinal central axis of the upper arm section 40. The main drive assembly 50 can be operated in any one of two directions to effect either internal or external rotation of a humerus bone in upper arm section 40 relative to the shoulder 16.

A secondary drive assembly 58 (FIGS. 1-3) is manually operable by the patient 14 to align the upper section 40 (FIG. 1) of the arm 20 of the patient 14 with the shoulder 16 of the patient. The secondary drive assembly 58 is operable in either one of two directions to effect either abduction or adduction of the arm 20.

The secondary drive assembly 58 is located beneath the armpit or axilla 34. The secondary drive assembly is positioned between the upper arm section 40 and the trunk 32 of the patient 14. The secondary drive assembly 58 is operable to move the upper arm section 40 into alignment with the shoulder 16 of the patient 14. The secondary drive assembly 58 is then effective to hold the upper arm section 40 in alignment with the shoulder 16.

In accordance with a feature of the present invention, the shoulder orthosis 10 (FIG. 1) obtains release of soft tissue in the shoulder 16 and/or arm 20 of the patient. The shoulder orthosis 10 effects elongation of viscoelastic tissue connected with the upper arm section 40 and the shoulder 16 of the patient. To effect stretching of the viscoelastic body tissue interconnecting the upper arm section 40 and shoulder 16, the main drive assembly 50 is operated to rotate the humerus bone 62 (FIG. 4) in the upper arm section 40 relative to the shoulder 16.

Operation of the main drive assembly 50 (FIG. 1) to rotate the humerus bone 62 (FIG. 4) is interrupted when the viscoelastic body tissue has been stretched to a maximum extent compatible with a patient's comfort level. The main drive assembly 50 is advantageously operated by the patient 14 himself/herself so that the patient can interrupt operation of the drive assembly when required in order to maintain patient comfort.

The main drive assembly 50 (FIG. 1) is constructed so that it continuously transmits force and is not operated in a reverse direction upon interruption of operation of the main drive assembly by the patient 14. This results in tension being maintained in the viscoelastic body tissue interconnecting the upper section 40 of the arm 20 of the patient 14 and the shoulder 16 when operation of the main drive assembly 50 is interrupted. When a sufficient period of time to enable the viscoelastic tissue to relax has elapsed, the patient 14 again operates the main drive assembly 50 to further stretch the viscoelastic body tissue connected with the upper arm section 40 and shoulder 16.

The shoulder orthosis 10 effects some distraction of the joint between the upper arm section 40 and shoulder 16. This distraction occurs due to the combined weight of the shoulder orthosis 10 and the arm 20.

Bones

Some of the bones in the body 12 of the patient 14 are illustrated in FIG. 4. The trunk 32 of the patient includes a shoulder joint 66 where the upper arm section 40 of the patient is connected with the trunk 32 of the patient. A head end portion 68 of the humerus bone 62 in the upper arm section 40 is connected with the trunk 32 at the shoulder joint 66. A radius bone 72 and an ulna bone 74 in the lower arm section 44 are connected with the opposite or lower end of the humerus bone 62.

The head end portion 68 of the humerus bone 62 is received in a glenoid cavity or fossa 80 formed in a scapula bone 82 at the shoulder joint 66. The scapula bone 82 articulates with the head end portion 68 of the humerus and the clavicle bone 84. The clavicle or collarbone 84 articulates with the sternum 86 and scapula bone 82. The scapula bone 82 is connected with rib bones 88 by body tissue.

The shoulder joint 66 is somewhat similar to a ball and socket joint. The head end portion 68 of the humerus bone 62 has a configuration which may be considered as being hemispherical. The glenoid cavity 80 forms a socket for the head end portion 68 of the humerus bone 62. However, the socket formed by the glenoid cavity 80 is shallow. Therefore, the glenoid cavity 80 may be considered as being a portion of a hemisphere.

It is well known that the head end portion 68 of the humerus bone 62 has an arcuate outer side surface which is not truly hemispherical in configuration. Similarly, the glenoid cavity 80 has a configuration which may be considered as being generally ovate. Since the head end portion 68 of the humerus bone 62 and the glenoid cavity 80 are not true hemispheres, the motion which occurs between the bones at the shoulder 16 during movement of the arm 20 is far more complicated than a simple ball and socket analogy.

A normal shoulder joint 66 which functions in a proper manner can accommodate movement in all directions. In order to obtain motion of the head end portion 68 of the humerus bone 62 without movement of the scapula bone 82 and/or clavicle bone 84, a longitudinal central axis of the humerus bone 62 should be aligned with a central portion of the glenoid cavity 80. When the humerus bone 62 is aligned with the glenoid cavity 80, the longitudinal central axis of the humerus bone extends through or close to the center of the glenoid cavity. At this time, an arcuately curving, generally hemispherical outer side surface 92 on the head end portion 68 of the humerus bone 62 is aligned with and is closely adjacent to a generally hemispherical side surface 94 of the glenoid cavity 80.

It should be understood that the outer side surface 92 on the head end portion 68 of the humerus bone 62 and the side surface 94 of the glenoid cavity 80 do not have truly hemispherical configurations and do not have centers of curvature which are exactly coincident when the head end portion 68 of the humerus bone 62 is aligned with the glenoid cavity 80. Therefore, there may be some shifting between the humerus bone 62 and the scapula bone 82 and/or clavicle bone 84 during rotation of the humerus bone 62 about its longitudinal central axis even though the longitudinal central axis of the humerus bone is aligned as close as is reasonably possible with the center of the glenoid cavity 80. In order to obtain stretching of viscoelastic body tissue interconnecting the head end portion 68 of the humerus bone 62 and the scapula bone 82 at the shoulder joint 66, movement of the scapula bone and/or clavicle bone 84 relative to the trunk 32 should be minimized during operation of the shoulder orthosis 10.

Lower Arm Section

The lower arm section 42 (FIGS. 2, 3 and 6) of the shoulder orthosis 10 is connected with the lower section 44 of the patient's arm 20 (FIG. 1). The lower arm section 42 of the shoulder orthosis 10 (FIGS. 2, 3 and 6) includes a first or lower cuff arm 102. The lower cuff arm 102 includes a straight rigid metal outer channel member 104 and a straight rigid metal inner channel member 106. The outer and inner channel members 104 and 106 are disposed in a telescopic relationship with each other and are interconnected by a fastener 108. When the fastener 108 is released, the outer channel member 104 and inner channel member 106 are longitudinally movable relative to each other to vary the extent of the lower arm section 42 of the orthosis 10.

A hand cuff 112 is disposed on the axially outer end portion of the outer channel member 104. The hand cuff 112 is disposed on a rigid circular metal base 114. The base 114 is fixedly connected with the outer channel member 104. A flexible hemisphere 118 (FIG. 6) is connected to the metal base 114 and engages a palm of a hand 46 (FIG. 1) of the patient. A strap 120 (FIGS. 2, 3 and 6) engages the back of the hand 46 of the patient. The strap 120 presses the palm of the patient's hand against the hemisphere 118. By loosening the fastener 108, the position of the hemisphere 118 relative to the inner channel member 106 can be varied to adjust the lower cuff arm 102 to accommodate patients having arms of different lengths.

The hemisphere 118 (FIGS. 2 and 6) has a radius which is sufficient to enable a portion of the palm of the patient's hand 46 (FIG. 1) to be further from the lower cuff arm 102 than a longitudinal central axis of the lower section 44 of the patient's arm 20. This results in the patient's hand 46 being held in a relaxed, cup-shaped configuration. By engaging the hemisphere 118, the patient's hand 46 is held against sidewise movement and the lower arm section 44 is stabilized on the lower arm section 42 of the orthosis 10.

Figure 2:
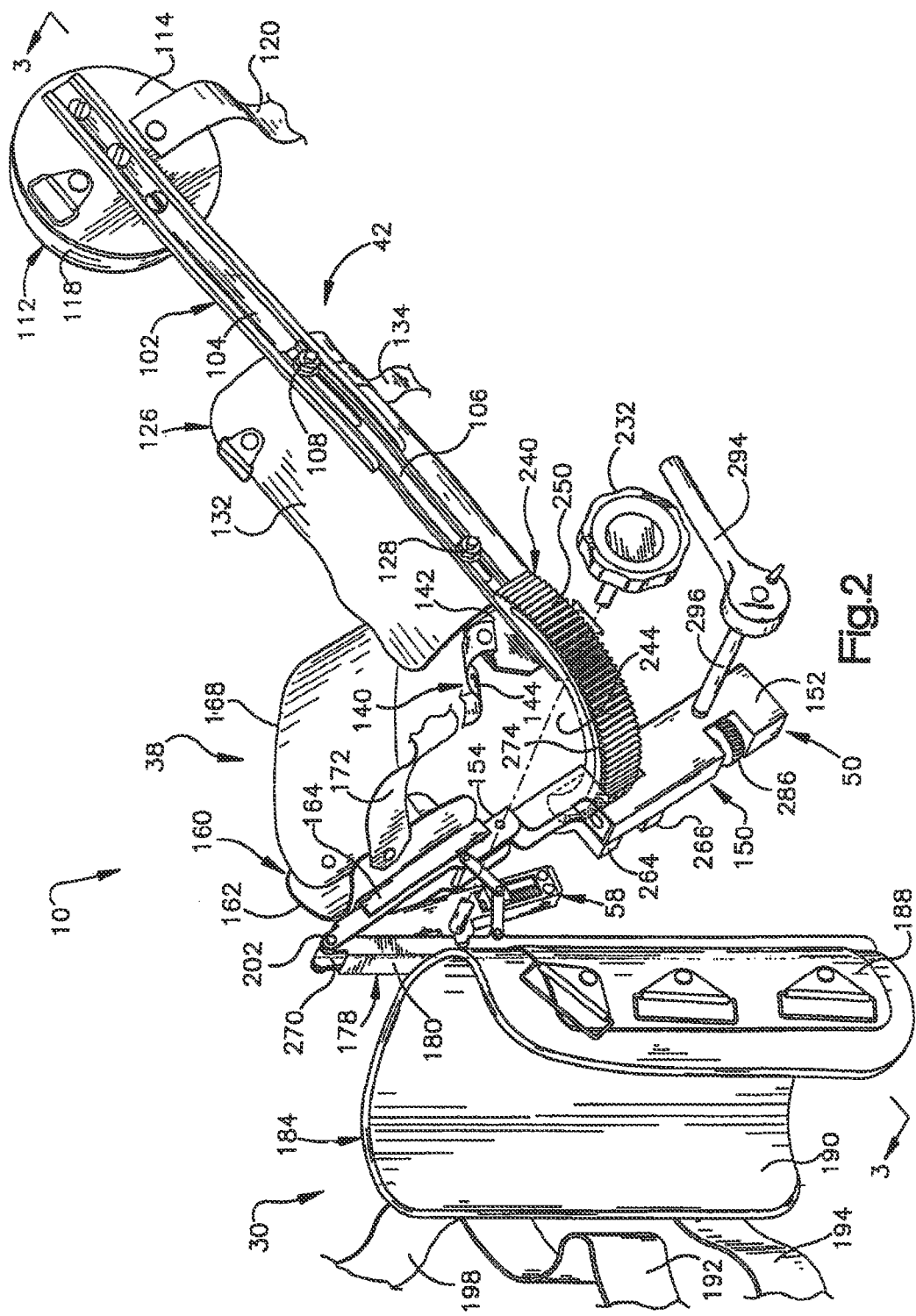
FIG. 2 is an illustration further depicting the construction of the shoulder orthosis of FIG. 1.
Figure 3:
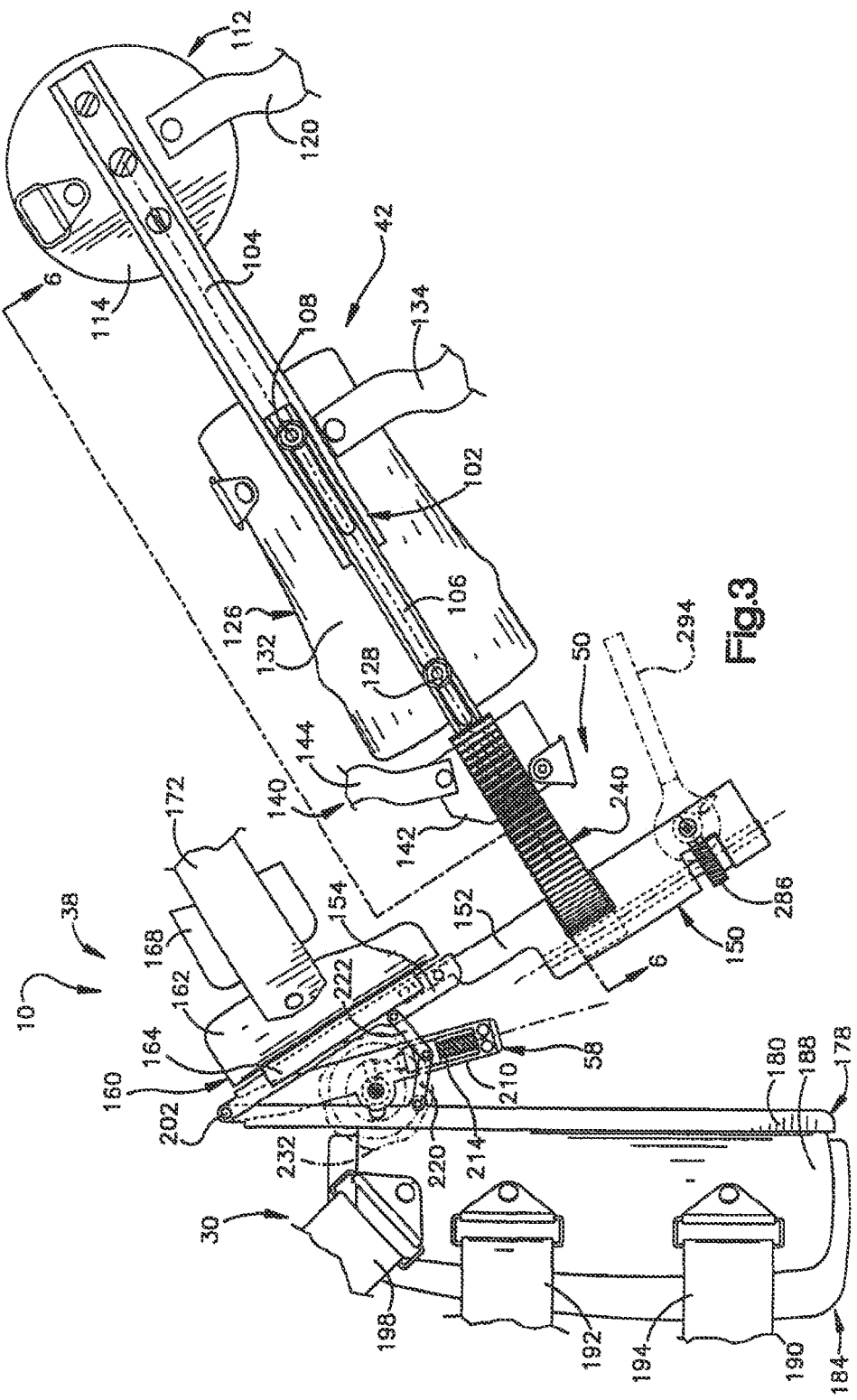
FIG. 3 is a front elevational view, taken generally along the line 3-3 of FIG. 2, further illustrating the construction of the shoulder orthosis.

A first or lower cuff 126 is connected with the inner channel member 106 by the fastener 108 and a second fastener 128 (FIGS. 2, 3 and 6). The lower cuff 126 includes a flexible polymeric body section 132 which is connected to the inner channel member 106 by the fasteners 108 and 128. The body section 132 extends part way around the lower arm section 44 of the patient 14 (FIG. 1). A central axis of the lower cuff 126 extends parallel to the lower cuff arm 102 and extends through the hemisphere 118 in the hand cuff 112.

A strap 134 (FIGS. 2, 3 and 6) is connected with the body section 132 and extends around the lower arm section 44 of the patient. Tightening the strap 134 causes the body portion 132 of the first or lower cuff 126 to flex inward and firmly grip the radius bone 72 and ulna bone 74 (FIG. 4) in the lower arm section 44 of the patient 14 (FIG. 1). Although one specific construction for the lower cuff 126 and hand cuff 112 is illustrated in FIGS. 2, 3 and 6, it is contemplated that these cuffs could have a different construction if desired.

In addition, the lower arm section 42 includes an elbow cuff 140 (FIGS. 2, 3 and 6) which is mounted on the inner channel member 106. The elbow cuff 140 includes a base plate 142 against which the elbow 54 (FIG. 1) in the arm 20 of the patient is pressed by a strap 144. When the strap 144 is tightened, the elbow 54 is firmly held against movement relative to the lower arm section 42. The elbow cuff 140 could have a different construction or could be omitted if desired.

The lower section 44 (FIG. 1) of the arm 20 of the patient 14 is firmly held against movement relative to the lower cuff arm 102 by three different cuffs. Thus, the hand cuff 112 holds the hand 46 of the patient 14 against movement relative to the lower cuff arm 102. The first or lower cuff 126 holds the lower arm section 44 of the arm 20 of the patient 14 against movement relative to the lower cuff arm 102. In addition, the elbow cuff 140 holds the elbow 54 of the patient 14 against movement relative to the lower cuff arm 102.

When the first or lower cuff 126 is connected with the lower section 44 of the arm 20 of the patient 14 and the hand cuff 112 is connected with the hand 46 of the patient (FIG. 1), a central axis of the lower section of the arm of the patient extends through the hemisphere 118. Force is transmitted between the hemisphere 118 and palm of the hand 46 of the patient during operation of the shoulder orthosis 10 to effect external rotation of the arm 20 of the patient. Similarly, force is transmitted between the strap 120 and the back of the hand 46 of the patient during operation of the shoulder orthosis 10 to effect internal rotation of the arm 20 of the patient.

Although specific constructions for the hand cuff 112, lower cuff 126 and elbow cuff 140 have been disclosed herein, it is contemplated that these cuffs could have a different construction if desired. For example, the base plate 142 of the elbow cuff 140 could be integrally formed as one piece with the body section 132 of the lower cuff. There are many other known cuff constructions which could be used in place of the specific cuff constructions disclosed herein. If desired, the lower cuff arm 102 could be formed as a portion of the lower cuff 126.

Upper Arm Section

The upper arm section 38 (FIG. 1) of the shoulder orthosis 10 is connected with the upper section 40 of the patient's arm 20. The upper arm section 38 (FIGS. 2, 3 and 5) includes a second or upper cuff arm 150. The upper cuff arm 150 has a longitudinal axis which extends perpendicular to a longitudinal axis of the lower cuff arm 102.

The second or upper cuff arm 150 includes a rigid straight metal lower channel member 152 (FIG. 5) and a rigid straight metal upper channel member 154. The lower and upper channel members 152 and 154 are telescopically adjustable relative to each other to accommodate patients having different length upper arm portions. Pin members 156 are provided to fixedly interconnect the lower and upper channel members 152 and 154 when the second or upper cuff arm 150 has been adjusted to a desired length.

Figure 5:
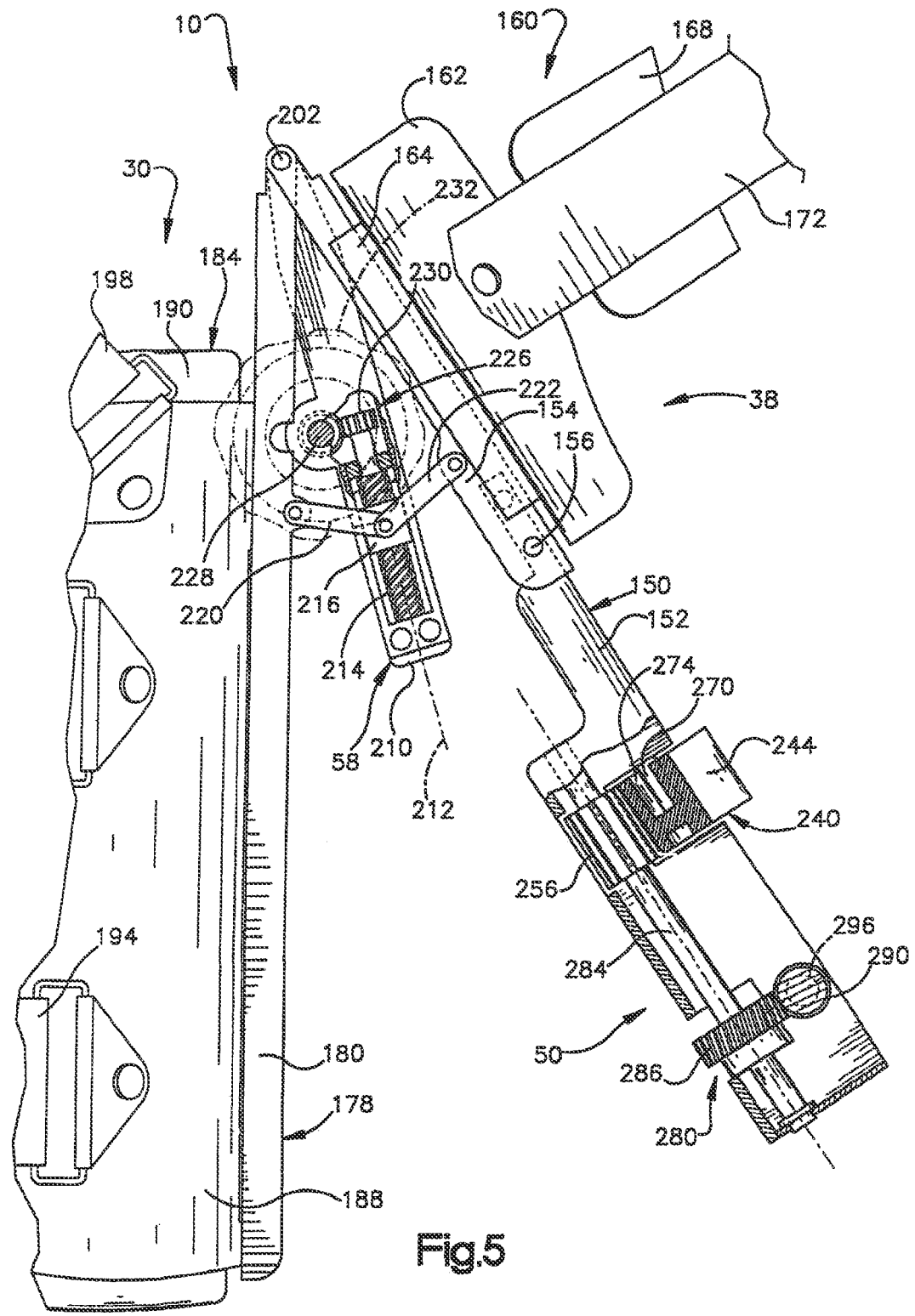
FIG. 5 is an enlarged fragmentary front elevational view of a portion of the shoulder orthosis of FIGS. 1-3, illustrating the manner in which a main and secondary drive assembly are connected with cuff arms.

The upper section 40 of the patient's arm 20 (FIG. 1) is connected with the second or upper cuff arm 150 by an upper cuff 160 (FIGS. 2, 3 and 5). The upper cuff 160 has a longitudinal central axis which extends perpendicular to and intersects a longitudinal central axis of the lower cuff 126. The upper cuff 160 includes a flexible polymeric body section 162. The body section 162 is fixedly connected to a connector channel 164. The connector channel 164 is fixedly connected to the upper channel member 154 of the upper cuff arm 150.

A flexible plastic tongue 168 (FIG. 2) is connected with the body section 162 of the upper cuff 160. A strap 172 is connected with the opposite side of the body section 162. The flexible tongue 158 is positioned in engagement with the upper section 40 of the patient's arm 20 (FIG. 1). The strap 172 is tightened to securely grip the upper section 40 of the patient's arm with the upper cuff 160.

Although one specific upper cuff 160 has been illustrated in FIGS. 2, 3 and 5, it is contemplated that the upper cuff 160 could have a different construction if desired. The upper cuff arm 150 could also have a construction which is different than the specific construction illustrated in the drawings. If desired, the upper cuff 160 could be constructed in such a manner as to enable the upper cuff arm 150 to be formed as a portion of the upper cuff.

Base Section

The base section 30 (FIGS. 1, 2 and 3) of the shoulder orthosis 10 is connected with and is held against movement relative to the trunk 32 (FIG. 1) of the patient. The base section 30 of the orthosis 10 includes a third or base cuff arm 178 (FIGS. 1, 2 and 3). The base cuff arm 178 is formed by a single rigid straight metal channel member 180.

A third or base cuff 184 is slidably connected with slots in the base cuff arm 178 by suitable fasteners (not shown). The fasteners enable the base cuff 184 to be released for movement axially along the base cuff arm 178 to position the base cuff 184 for engagement with the trunk 32 of different size patients 14. The base cuff 184 includes a body section 188 which is formed of a flexible polymeric material. A pad 190 is connected with the body section 188. The body section 188 and pad 190 grip the trunk 32 of the patient at a location below the arm pit or axilla 34 (FIG. 1).

The body section 188 of the third or base cuff 184 is connected with the trunk 32 of the patient 14 by a pair of generally horizontal straps 192 and 194 (FIG. 1). The straps 192 and 194 extend around the trunk 32 of the patient and are connected with opposite sides of the body section 188 of the base cuff 184. A shoulder strap 198 extends across the shoulder 24 to hold the body section 188 of the base cuff 184 in position on the trunk 32 of the patient 14. The straps 192, 194, and 198 cooperate with the body section 188 of the base cuff 184 to hold the base cuff stationary on the trunk 32 of the patient 14.

The base cuff arm 178 and the second or upper cuff arm 150 are interconnected at a pivot connection 202 (FIGS. 1, 2, 3 and 5). The pivot connection 202 enables the upper cuff arm 150 to pivot about an axis which extends perpendicular to and intersects longitudinal central axes of the base cuff arm 178 and the second or upper cuff arm 150. The pivot connection 202 is positioned immediately beneath the armpit or axilla 34 (FIG. 1) on the body 12 of the patient 14. The pivot connection 202 enables the upper arm section 38, main drive assembly 50, and lower arm section 42 to be moved as a unit relative to the base section 30 of the orthosis 10 by operation of the secondary drive assembly 58.

The base cuff 184 could have a construction which is different than the specific construction disclosed herein. For example, the base cuff 184 could be integrally formed as one piece with the upper cuff 160. If desired, the base cuff arm 178 could be formed as a portion of the base cuff 184.

Secondary Drive Assembly

The secondary drive assembly 58 (FIG. 1) moves the upper arm section 40 and the lower arm section 44 of the arm 20 of the patient 14 relative to the shoulder 16. The secondary drive assembly 58 is operated to align the central axis of the humerus bone 62 (FIG. 4) in the upper arm section 40 with the center of the glenoid cavity 80 in the scapula bone 82. The secondary drive assembly 58 may be operated by either a therapist or the patient 14. In order to promote patient confidence, it may be preferred to have the patient 14 operate the secondary drive assembly under the instruction of a therapist.

When the central axis of the humerus bone extends through a central portion of the glenoid cavity 80, the humerus bone 62 can be rotated about its central axis while the scapula bone 82 and clavicle bone 84 remain substantially stationary relative to the trunk 32 of the patient 14. This is because when the humerus bone 62 is aligned with the center of the glenoid cavity 80, the central axis of the humerus bone 62 extends through a center of curvature of an arcuate surface 92 on the head end portion 68 of the humerus bone 62 and through a center of curvature of an arcuate surface 94 of the glenoid cavity 80.

To move the humerus bone 62 into alignment with the glenoid cavity 80, the secondary drive assembly 58 includes a rectangular tower or base frame 210 (FIG. 5). The tower or base frame 210 extends downward from the pivot connection 202 between the base cuff arm 178 and the second or upper cuff arm 150. The base cuff arm 178 and second or upper cuff arm 150 are pivotal toward and away from the tower 210 about the pivot connection 202.

The tower 210 has a central axis 212 (FIG. 5) which bisects an angle formed between the longitudinal central axis of the base cuff arm 178 and the longitudinal central axis of the second or upper cuff arm 150. The longitudinal central axis 212 of the tower 210 intersects and extends perpendicular to the axis about which the base cuff arm 178 and second or upper cuff arm 150 are pivotal at the pivot connection 202.

The secondary drive assembly 58 includes a screw 214 (FIG. 5) having a central axis which is coincident with the central axis 212 of the tower 210. The screw 214 is rotatably supported in the tower 210 by suitable bearings. The screw 214 has an external thread which engages an internal thread on an actuator block 216. The cooperation between the external thread on the screw 214 and the internal thread between the actuator block 216 results in the actuator block moving toward or away from the pivot connection 202 during rotation of the screw 214 about its central axis.

A pair of identical links 220 and 222 (FIG. 5) extend between the actuator block 216 and the cuff arms 178 and 150. As the actuator block 216 is moved axially along the screw 214, the links 220 and 222 maintain the actuator block and the screw 214 centered midway between the cuff arms 178 and 150. Although only a single pair of links 220 and 222 are shown in FIG. 5, it should be understood that a second pair of links having the same construction as the links 220 and 222 are connected with the rear or posterior side of the actuator block 216 and the cuff arms 178 and 150. The links on the posterior or rear side of the actuator block 216 are aligned with the links 220 and 222 on the front or anterior side of the actuator block.

A manually operable drive assembly 226 (FIG. 5) is connected with the screw 214. The drive assembly 226 includes a worm 228 which engages a gear 230. The gear 230 is fixedly connected with the screw 214. The worm 228 is rotatable about an axis which extends perpendicular to coincident central axes of the gear 230 and screw 214.

Manual rotation of an input member or knob 232 (FIGS. 1 and 2) rotates the worm 228 (FIG. 5) and the gear 230. Rotation of the gear 230 rotates the screw 214. Rotation of the screw 214 moves the actuator block 216 either toward or away from the pivot connection 202. When the actuator block 216 is moved toward the pivot connection 202 by the screw 214, the base cuff arm 178 and upper cuff arm 150 are pivoted away from each other by the links 220 and 222. When the actuator block 216 is moved away from the pivot connection by the screw 214, the base cuff arm 178 and upper cuff arm 150 are pivoted toward each other by the links 220 and 222.

The input member 232 can be manually rotated by the patient 14 to adjust the extent of abduction of the arm 20 (FIG. 1) to a position of greatest comfort. The position of greatest comfort will correspond to the position in which the longitudinal central axis of the humerus bone 62 (FIG. 4) is aligned with the center of the glenoid cavity 80.

The secondary drive assembly 58 (FIG. 5) is constructed so that once the angle between the upper cuff arm 150 and the base cuff arm 178 has been adjusted by operation of the secondary drive assembly, the angle between the cuff arms is maintained constant. Thus, the secondary drive assembly is constructed so that force applied to the base cuff arm 178 and upper cuff arm 150 cannot actuate the secondary drive assembly 58 to change the angle between the cuff arms. Therefore, once the central axis of the humerus bone has been aligned with the center of the glenoid cavity 80 by operation of the secondary drive assembly 58, the humerus bone 62 is maintained in alignment with the center of the glenoid cavity.

The secondary drive assembly 58 has a construction which is generally similar to the construction of a drive assembly disclosed in U.S. Pat. No. 5,285,773. If desired, the secondary drive assembly 58 could have a different construction. For example, the secondary drive assembly 58 could be constructed in a manner similar to that disclosed in U.S. Pat. No.

5,503,619. Of course, other known drive assemblies could be substituted for the specific secondary drive assembly 58 illustrated in FIG. 5.

Main Drive Assembly

The main drive assembly 50 (FIGS. 2 and 5) interconnects the upper cuff arm 150 and the lower cuff arm 102. The arm 20 (FIG. 1) of the patient 14 is bent at a 90.degree. angle at the elbow 54. This allows upper section 20 of the patient's arm 20 to extend along the upper cuff arm 150. The lower section 44 of the patient's arm 20 extends along the lower cuff arm 102. The elbow 54 and adjacent portions of the patient's arm 20 extend through the main drive assembly 50.

The main drive assembly 50 is operable to effect either internal or external rotation of the humerus bone 62 (FIG. 4) in the upper arm section 40 of the arm 20 relative to the shoulder joint 66 and scapula bone 82. Operation of the main drive assembly 50 rotates the humerus bone 62 about its longitudinal central axis. To effect rotation of the humerus bone 62, the main drive assembly 50 pivots the lower cuff arm 102 and lower section 44 of the patient's arm 20 about the longitudinal central axis of the humerus bone. The upper cuff arm 150 and base cuff arm 178 are stationary relative to each other and the trunk 32 of the patient 14 during operation of the main drive assembly 50 and movement of the lower cuff arm 102.

When the main drive assembly 50 is operated to rotate the humerus bone 62 about its longitudinal central axis, the secondary drive assembly 58 will have previously been adjusted to align the longitudinal central axis of the humerus bone with the center of the glenoid cavity 80. Therefore, when the humerus bone 62 is rotated about its central axis, there is no substantial movement of the scapula bone 82 and/or clavicle bone 84 relative to each other and the trunk 32 of the patient 14. It should be understood that the main drive assembly 50 is not operated to rotate the humerus bone 62 until after the secondary drive assembly 58 has been operated to position the humerus bone in alignment with the glenoid cavity 80.

The main drive assembly 50 includes a main gear or drive member 240 which is fixedly connected with the lower cuff arm 102 (FIGS. 3 and 6). The main gear or drive member 240 is rotatably connected with the upper cuff arm 150. When the orthosis 10 is positioned on the arm 20 of a patient 14, in the manner illustrated in FIG. 1, the arm of the patient extends through an opening 244 (FIGS. 2 and 6) in the main gear 240. Thus, the elbow 54 (FIG. 1) is disposed in the opening 244 (FIG. 6) in the main gear 240. The elbow cuff 140 holds the elbow in position relative to the main gear 240 and lower cuff arm 102.

Although the elbow 54 is shown in FIG. 1 as being disposed in the opening 244 in the main gear 240, a different portion of the arm 20 of the patient 14 could be disposed in the opening if desired. Furthermore, it is contemplated that the main gear 240 could be offset to one side, for example, downward, of the elbow 54 and rotatably connected with the upper cuff arm 150. If this was done, the arm 20 of the patient 14 would not extend through the main gear 240 and the opening 244 could be eliminated. However, it is preferred to have the main gear 240 as close as possible to the elbow 54 and lower cuff arm 102 to promote efficient transfer of force between the main drive assembly 50 and the arm 20 of the patient 14.

The main gear 240 includes an arcuate array 248 (FIG. 6) of gear teeth 250. The arcuate array 248 of gear teeth has a configuration of a portion of a circle. The central axis of the main gear 240 extends parallel to the longitudinal central axis of the upper cuff arm 150 and is coincident with a longitudinal central axis of the upper section 40 (FIG. 1) of the arm 20 of the patient. The opening 244 extends between opposite ends of the arcuate array 248 of gear teeth 250 to enable the arm 20 (FIG. 1) of the patient 14 to be readily moved into the opening in the main gear.

The inner channel member 106 (FIG. 6) of the lower cuff arm 102 extends into the opening 244. The inner channel member 106 is fixedly connected with the main gear 240 by suitable fasteners (not shown) which extend through the base plate 142 of the elbow cuff 140. The inner channel member 106 is fixedly connected to the main gear 240 with a central axis of the inner channel member extending perpendicular to the parallel central axes of the main gear and upper cuff arm 150. Since the lower cuff arm 102 is fixedly connected with the main gear 240, the lower cuff arm rotates with the main gear relative to the upper cuff arm 150.

When the arm 20 of the patient 14 is positioned in the upper cuff 160, opening 244 in the main gear 240, and lower cuff 126, in the manner illustrated in FIG. 1, the central axis of the humerus bone 62 is substantially coincident with a central axis of the arcuate array 248 of gear teeth 250 (FIG. 6). The central axis of the lower section 44 (FIG. 1) of the patient's arm 20 intersects the central axis of the upper section 40 of the patient's arm at a right angle at the elbow 54. The intersection of the central axis of the upper section 40 and lower section 44 of the patient's arm 20 is disposed in a central portion of the opening 244 in the main gear 240. When the main gear 240 and lower cuff arm 102 are rotated about the central axis of the main gear, the humerus bone 62 (FIG. 4) in the upper section 40 of the arm 20 of the patient is rotated about its central axis.

The main gear 240 is disposed in meshing engagement with a pinion gear 256 (FIGS. 5 and 6). The pinion gear 256 is rotatably mounted on the upper cuff arm 150.

The main gear 240 is supported for rotation about the central axis of the opening 244 and the central axis of the upper arm section 40 of the arm 20 (FIG. 1) of the patient 14 by a positioning assembly 262 (FIG. 7). The positioning assembly 262 is disposed on the anterior or back side of the main cuff arm 150. The positioning assembly 262 includes a pair of guide blocks 264 and 266 (FIG. 7) which engage axially opposite sides of the main gear 240.

The guide blocks 264 and 266 are fixedly mounted on the upper cuff arm 150. A pair of parallel pins 270 and 272 extend from the guide block 262 into an arcuate groove 274 (FIGS. 6 and 7) formed in the main gear 240. The pins 270 and 272 extend into the arcuate groove 274 to guide rotational movement of the main gear 240 relative to the upper cuff arm 150 upon rotation of the pinion gear 256 (FIG. 6). Although a groove 274 (FIG. 7) is formed in only one side of the main gear 240 and pins 270 and 272 extend from only the guide block 264, it is contemplated that a second groove could be formed in the axially opposite side of the main gear 240 and be engaged by pins extending from the guide block 266 if desired.

It should be understood that a different mounting arrangement could be utilized for supporting the main gear 240. Thus, rather than having the arcuate groove 274, a pair of arcuate ribs could be provided on opposite sides of the main gear. These ribs would extend into arcuate tracks formed in the guide blocks 264 and 266. By having the support for the main gear 240 offset from the central axis of the main gear, it is possible to have a portion of the arm 20 (FIG. 1) of the patient 14 extend into the opening 244 (FIG. 2) through the central portion of the main gear 240. However, the main gear 240 could be offset to one side of the arm of the patient and could be rotatably supported at its center if desired.

To rotate the main gear 240 and lower cuff arm 102 relative to the second or upper cuff arm 150, the pinion gear 256 is rotated by a pinion drive 280 (FIG. 5). The pinion drive 280 includes a drive shaft 284 (FIG. 5) which is fixedly connected with the pinion gear 256. A second pinion gear 286 is fixedly connected to the drive shaft 284 in a coaxial relationship with the pinion gear 256. A worm 290 is disposed in meshing engagement with the second pinion gear 286.

The worm 290 is driven by a reversible ratchet 294 (FIG. 2). The reversible ratchet 294 is connected with the worm 290 by an input shaft 296. The ratchet 294 extends in the anterior direction, that is frontward, from the upper cuff arm 150. This enables the ratchet 294 to be manually operated by the patient 14.

The patient operates the main drive assembly 50 by actuating the ratchet 294 under the influence of force transmitted from the right arm 22 (FIG. 1) of the patient to the ratchet 294. Of course, a therapist may assist in operation of the ratchet 294 if desired. The reversible ratchet 294 can be actuated to rotate the main gear 240 in either one of two directions to effect either internal or external rotation of the humerus bone 62 in the upper arm section 40 of the patient 14.

Mounting and Operation of the Orthosis

When the orthosis 10 is to be mounted on the patient 14, the straps 192, 194, and 198 for the base cuff 184 (FIG. 1), a strap 144 for the elbow cuff 440, the strap 134 for the lower cuff 126, and the strap 120 for the hand cuff 112 are all released in the manner illustrated in FIG. 2. The body section 188 of the base cuff 184 is then positioned in engagement with the trunk 32 of the patient 14. The straps 192, 194 and 198 are then pulled only tight enough to loosely hold the base cuff 184 in position on the trunk 32 of the patient. At this time, the connection 202 between the base cuff arm 178 and the upper cuff arm 150 is disposed approximately one inch below the arm pit or axilla 34 (FIG. 1) of the patient 14.

Contemporaneously with positioning of the base cuff 184 on the trunk 32 of the patient, the arm 20 of the patient is positioned in the upper cuff 160 and the lower cuff 126. The elbow of the patient is positioned in the elbow cuff 140. The lower cuff 126 is then tightened to grip the lower arm section 44. The elbow cuff 140 and the hand cuff 112 are then tightened. The upper cuff 160 is then tightened.

Once the various cuffs have been tightened to secure the shoulder orthosis 10 to the arm 20 of the patient, the orthosis is adjusted so that the patient's shoulder is 30 degrees scapular plane. The upper arm 40 of the patient extends forward at an angle of approximately 30.degree. The straps 192, 194 and 198 are then tightened to hold the shoulder orthosis 10 firmly in place.

The input knob 232 of the secondary drive assembly 58 is then actuated to a plane approximately 45.degree. of abduction of the shoulder 16 of the patient. At this time, the arm 20 is positioned in the plane of the scapula. The aforementioned steps may be performed by the patient alone or by the patient with the help of a therapist.

Once the upper section 40 of the arm 20 of the patient has been positioned in alignment with the shoulder 16 by operation of the secondary drive assembly 58, the patient operates the main drive assembly 50 to effect either external or internal rotation of the humerus bone 62 in the upper section 40 of the arm 20. To actuate the main drive assembly 50, the patient 14 manually rotates the ratchet 294 (FIG. 2).

Rotation of the ratchet 294 rotates the worm 290 and drive shaft 284. Rotation of the drive shaft 284 rotates the pinion gear 256 and main gear 240. As the main gear 240 is rotated relative to the upper cuff arm 150, the humerus bone 62 is rotated about its central axis. Rotation of the humerus bone 62 stretches viscoelastic tissue in the shoulder joint 66.

When the patient 14 has operated the main drive assembly 50 to a maximum extent compatible with comfort of the patient, operation of the main drive assembly is interrupted. The drive arrangement between the worm 290 and second gear 286 is such that force transmitted from the lower arm section 44 through the lower cuff arm 102 to the main gear 50 is ineffective to rotate the main gear relative to the upper cuff arm 150. Therefore, tension is maintained in the viscoelastic body tissue connected with the head end portion 68 of the humerus bone 62 even though operation of the main drive assembly 50 is interrupted.

Immediately after operation of the main drive assembly is interrupted, the stretched viscoelastic body tissue connected with the humerus bone 62 begins to relax. With the passage of a relatively short interval of time, for example fifteen minutes, the viscoelastic body tissue will have relaxed sufficiently to enable the patient 14 to again operate the main drive assembly 50 to further stretch the viscoelastic tissue. As the patient operates the main drive assembly 50 to further stretch the viscoelastic body tissue, the main gear 240 and the lower cuff arm are rotated relative to the upper cuff arm 150.

When the patient has again reached the limit of his level of comfort, operation of the drive assembly 50 is interrupted. The process of operating and interrupting the operation of the main drive assembly 50 is repeated to obtain a gradual stretching of the viscoelastic tissue connected with the humerus bone 62. Since the patient is in full control of the operation of the main drive assembly 50, the patient determines the extent of the stretching of the viscoelastic body tissue.

When the viscoelastic body tissue has been repeatedly stretched to the maximum extent allowed by the comfort level of the patient, the shoulder orthosis 10 is removed from the body 12 of the patient 14. To do this, the direction of operation of the ratchet 294 is reversed and the main drive assembly 50 operated to release the pressure against the lower section 44 of the arm 20 of the patient. Once this has been done, the various cuffs are loosened and the orthosis 10 is removed from the patient until the next treatment is undertaken.

CONCLUSION

A new and improved apparatus 10 for effecting relative movement between bones in a body 12 of a patient 14 includes a first cuff 126 which grips a lower portion 44 of an arm 20 of the patient. A second cuff 160 grips an upper portion 40 of the arm 20 of the patient. A drive assembly 50 is operable to rotate the first cuff 126 and a humerus bone 62 in the arm 20 of the patient 14 about a central axis of the humerus bone. This results in a stretching of viscoelastic tissue connected with a head end portion 68 of the humerus bone 16.

The extent of stretching of the viscoelastic tissue connected with a humerus bone 62 in the arm 20 of the patient 14 may be maximized by interrupting operation of the drive assembly 50 to allow the viscoelastic body tissue to relax. After the viscoelastic body tissue has relaxed, the drive assembly 50 is again operated to further rotate the first cuff 126 and further stretch the viscoelastic body tissue connected with the humerus bone 62.

A secondary drive assembly 58 is provided to pivot the humerus bone 62 in the arm 20 of the patient 14 about the head end portion 68 of the humerus bone. This moves an arcuate surface 92 on the head end portion 68 of the humerus bone 62 into alignment with an arcuate surface 94 of a glenoid cavity 80 in a scapula bone 82 in the shoulder 16 of the patient 14. The secondary drive assembly 58 is disposed beneath an axilla 34 between the trunk 32 and arm 20 of the patient 14.

The invention claimed is:

1. A shoulder orthosis configured to stretch viscoelastic tissue at a shoulder joint of a patient comprising:
    an upper arm section configured to be coupled to an upper portion of the arm of the patient;
    a lower arm section coupled to the upper arm section, the lower arm section configured to be coupled to a lower portion of the arm of the patient;
    a drive assembly interconnecting the upper and lower arm sections, the drive assembly configured to:
        rotate the lower arm section with respect to the upper arm section about a longitudinal axis of the upper arm section to effect at least one of internal and external rotation of the upper portion of the arm of the patient at the shoulder joint; and
        prevent counter-rotation of the lower arm section with respect to the upper arm section about the longitudinal axis of the upper arm section to hold at least one of internal and external rotational positions of the upper portion of the arm of the patient;
    a base section configured to be coupled to a trunk of the patient, wherein the upper arm section is rotatable relative to the base section to adjust an angle defined between the upper arm section and the base section; and
    a second drive assembly interconnecting the upper arm section and the base section and configured to rotate the upper arm section relative to the base section.

2. A shoulder orthosis in accordance with claim 1, wherein the lower arm section is oriented to be substantially orthogonal to the upper arm section.

3. A shoulder orthosis in accordance with claim 1, wherein the drive assembly comprises a drive gear that is substantially parallel to the upper arm section.

4. A shoulder orthosis in accordance with claim 1, wherein the drive assembly comprises an arcuate array of gear teeth.

5. A method of assembling a shoulder orthosis, the method comprising:
    coupling a lower arm section to an upper arm section, the lower arm section configured to be coupled to a lower portion of an arm of a patient, and the upper arm section configured to be coupled to an upper portion of the arm of the patient; and
    operably coupling a drive assembly to the upper arm section and the lower arm section, the drive assembly configured to:
        rotate the lower arm section with respect to the upper arm section about a longitudinal axis of the upper arm section to effect at least one of internal and external rotation of the upper portion of the arm of the patient at the shoulder joint; and
        prevent counter-rotation of the lower arm section with respect to the upper arm section about the longitudinal axis of the upper arm section to hold at least one of internal and external rotational positions of the upper portion of the arm of the patient.

6. A method in accordance with claim 5, wherein said coupling a lower arm section to an upper arm section comprises coupling the lower arm section to the upper arm section, such that the lower arm section is oriented to be substantially orthogonal to the upper arm section.

7. A method in accordance with claim 5, wherein said operably coupling a drive assembly comprises coupling the drive assembly to the lower arm section, such that a drive gear of the drive assembly is substantially parallel to the upper arm section.

8. A method in accordance with claim 5, wherein the drive assembly includes an arcuate array of gear teeth.

9. A method in accordance with claim 5, further comprising:
    coupling a base section to the upper arm section, the base section configured to be coupled to a trunk of the patient;
    operably coupling a second drive assembly to the upper arm section and the base section, such that the upper arm section is rotatable to adjust an angle defined between the upper arm section and the base section.

10. A method of stretching viscoelastic tissue at a shoulder joint using a shoulder orthosis, the method comprising:
    coupling an upper arm section of the shoulder orthosis to an upper portion of an arm of a patient;
    coupling a lower arm section of the shoulder orthosis to a lower portion of the arm of the patient; and
    operating a drive assembly to rotate the lower arm section with respect to the upper arm section about a longitudinal axis of the upper arm section to effect one of internal and external rotation of the upper portion of the arm of the patient at the shoulder joint, and to prevent counter-rotation of the lower arm section with respect to the upper arm section about the longitudinal axis of the upper arm section to hold at least one of internal and external rotational positions of the upper portion of the arm of the patient.

11. A method in accordance with claim 10, further comprising:
    operating a second drive assembly coupled to the upper arm section to adjust an angle defined between the upper arm section and the base section.

* * * * *